Figure 1:
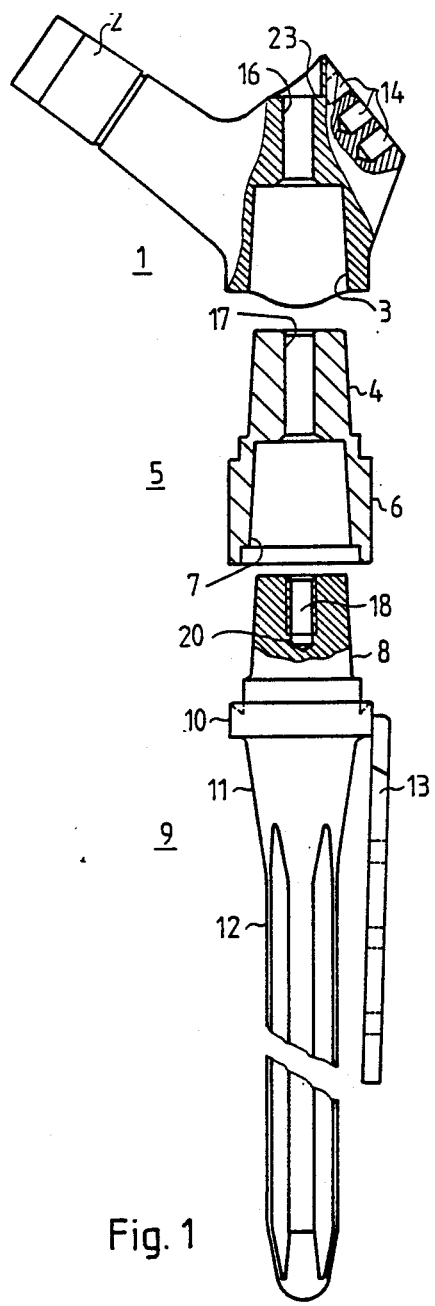

United States Patent [19]

Kranz et al.

[11] Patent Number: 4,878,917
[45] Date of Patent: Nov. 7, 1989

[54] MODULAR ASSEMBLY FOR A SHAFT PROSTHESIS

[75] Inventors: Curt Kranz; Emmanuel Anapliotis, both of Berlin, Fed. Rep. of Germany

[73] Assignee: Mecron medizinische Produkte GmbH, Berlin, Fed. Rep. of Germany

[21] Appl. No.: 41,378

[22] Filed: Apr. 23, 1987

[30] Foreign Application Priority Data

Apr. 25, 1986 [DE] Fed. Rep. of Germany ... 8611697[U]

[51] Int. Cl.$^4$ .............................................. A61F 2/30
[52] U.S. Cl. ..................................................... 623/18
[58] Field of Search ....................... 623/16, 20, 22, 23, 623/18

[56] References Cited

U.S. PATENT DOCUMENTS

| | | | |
|---|---|---|---|
| 3,846,846 | 11/1974 | Fischer | 623/23 |
| 3,987,499 | 10/1976 | Scharbach et al. | 623/23 |
| 4,051,559 | 10/1977 | Pifferi | 623/23 |
| 4,693,724 | 9/1987 | Rhenter et al. | 623/23 |

FOREIGN PATENT DOCUMENTS 3336005 4/1985 Fed. Rep. of Germany ........ 623/23

Primary Examiner—Richard J. Apley
Assistant Examiner—David J. Isabella
Attorney, Agent, or Firm—Spencer & Frank

[57] ABSTRACT

A modular assembly for a shaft prosthesis having a head part and an end part, of which one part has a conical protrusion and the other part has a conical bore, wherein between these two parts at least one intermediate part adapted to the protrusion and/or bore is provided, wherein the head part (1) and/or at least one intermediate part (5) has a through bore (16) and the end part (9) or an intermediate part (5) has a bore (17 or 18) having means (20) for releasable engagement for the sake of transmitting a force in the axial direction wherein when the parts (1, 5 and/or 9) have been joined the bores (16-18) are axially aligned with respect to one another in the direction of the shaft, and a tension rod (15) is provided with and is connectable with an engagement element for releasable engagement, and when the prosthesis parts have been joined together projects beyond the head part (1) at least when the head and end parts have been joined together. For anchoring long modular prosthesis assemblies, the end part (9) has an adjusting device (15, 40), with which movable shaft parts (32, 3) of the end part (9) can be forced apart after the insertion of the shaft prosthesis and can be clamped to the medullary cavity wall of the bone receiving the shaft.

6 Claims, 4 Drawing Sheets

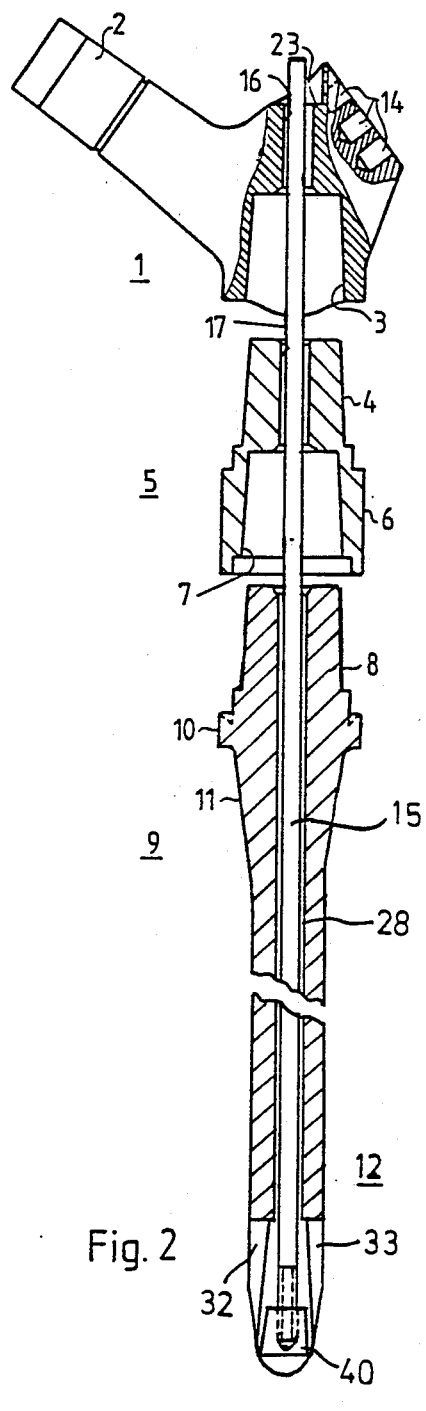
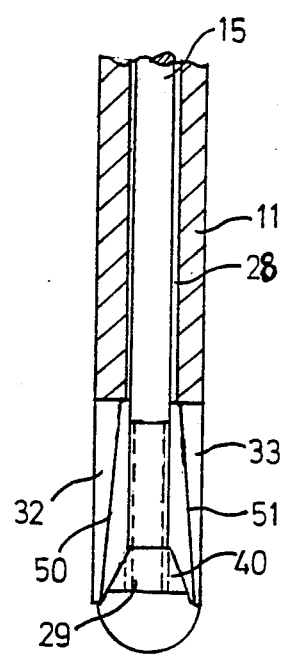
Fig. 2
Fig. 3

FIG. 6  FIG. 7  FIG. 8
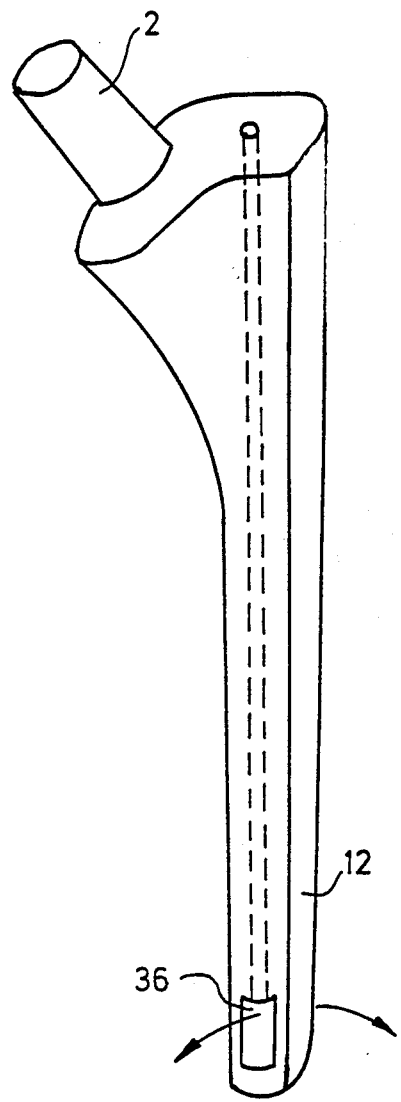
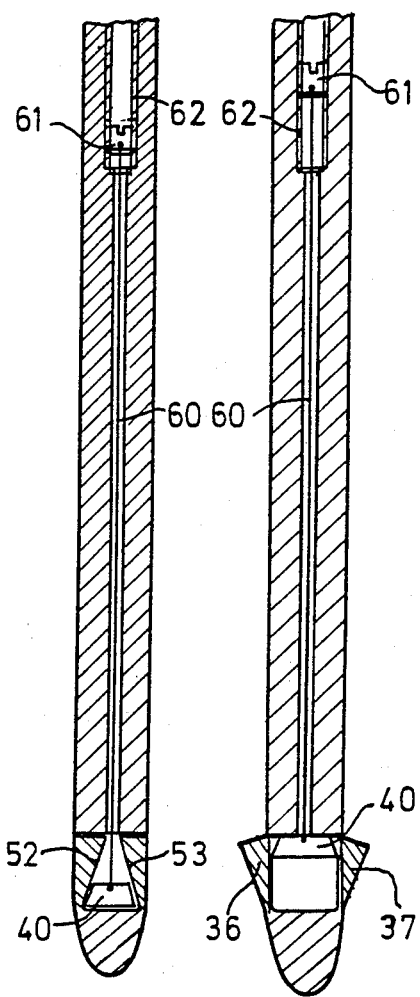

MODULAR ASSEMBLY FOR A SHAFT PROSTHESIS

The invention relates to a modular assembly for a shaft prosthesis.

A modular assembly of this kind is known from German patent disclosure document DE-OS 32 05 577. The component parts described there can be fitted together to make a femoral prosthesis of a desired length, and when assembled make a relatively rigid, linearly extending femoral replacement.

The known shaft prosthesis has the disadvantage that when the assembled prosthesis is implanted, loosening of the connecting elements (male and female cones) occurs, which presents the possible danger of relative rotation of the individual parts about the longitudinal axis of the shaft.

The object of the invention is to provide a way of subsequently connecting the individual parts of the prosthesis securely with one another by compression, so that the parts will remain securely connected to one another even with the impacts and the like that occur during use.

In particular, however, it is favorable that the tension rod used for seating the connecting cones can be removed entirely from the prosthesis shaft once the firm connection has been made, so that no parts are left there that could loosen or that would have undesirable reactions with body fluids. With the tension rod according to the invention, any arbitrary number of successive elements can be connected to one another, so that even when re-operations are done, an intermediate part that needs to be introduced can be secured by the same principle, without having to remove the end.

In a preferred embodiment of the invention, the tension rod is selected to be long enough that even with the maximum number of elements to be joined, it projects from the top part of the prosthesis to such an extent that after its end is detached the remaining end of the shaft can be grasped, unscrewed and removed from the prosthesis. For connecting the tension rod to the last prosthesis element (that is, the one located at the greatest depth), connections of the type that enable the transmission of tensile forces are suitable. These include, in particular, screw threads, bayonet couplings or spreadable ends of the tension rod, which engage parts of the surface that are transverse to the tension direction from behind, in the manner of barbed hooks.

A sheath of variable length enables the transmission of compressive forces into the top part of the prosthesis (or the uppermost prosthesis element to be connected), and the end of the sheath serves as an abutment for forces to be exerted upon the tension rod. A nut or slidably shaped tongs are suitable means for exerting tensile forces. The end of the tension rod that at first remains in the prosthesis shaft after detachment of the other end of the tension rod above the predetermined breaking point has a thread having a spiral direction oriented contrary to the loosening direction of the thread, etc., provided in the bottom prosthesis element that is to be connected, so that when a loosening tool having a female thread is screwed on, the end of the tension rod in the lowermost part of the prosthesis is loosened by unscrewing.

An advantageous further development of the invention provides that the end part has an adjusting device with which movable elements of the end part, after insertion of the modular shaft prosthesis assembly, can be forced apart and be clamped to the medullary cavity wall of the bone receiving the shaft.

Accordingly, a modular prosthesis assembly can be used even for very long shaft prostheses, and the modular prosthesis assembly can be implanted accurately and in a torsionally secured manner, and in the implanted state it can be adapted to variable cross sections of the medullary cavity of the bone receiving the shaft, so that it can be firmly anchored in the medullary canal, yet at the same time it remains possible, in the event that reimplantation becomes necessary, to loosen the modular prosthesis assembly from the medullary canal easily and without substantial damage to the bone.

In a further feature of the provision according to the invention, the movable elements of the inner part comprise elements with a variable cross section in the axial direction that are capable of being spread apart; a bolt or wedge which is movable in the axial direction via a tensioning element disposed in the through bore is disposed between these elements, so that when an axial force is exerted upon the bolt or wedge, the elements are spread apart. The connection of the tensioning element with the bolt or wedge can be permanent or may be embodied as a screw thread connection, bayonet coupling or the like. The spreading direction of the spreadable elements may be disposed in the direction of insertion of the shaft prosthesis, or contrary to it, depending on the type and length of shaft prosthesis used and depending on the shape of the medullary canal, so that the spreadable elements either press against the widening wall of the medullary cavity or become anchored in the medullary canal in the manner of barbed hooks.

A further advantageous feature of the provision according to the invention provides that the movable elements of the end part comprise resilient elements that are joined to one another at the upper and lower end of the end part, and that the tensioning element can be secured on the lower end of the resilient elements in such a way that the resilient elements can be flexed apart when the tensioning element moves in the axial dirction.

Advantageous further developments of the invention are defined in the dependent claims and will be described in further detail below, together with the description of the preferred embodiment of the invention, referring to the figures shown in the drawing.

Figure 1A:
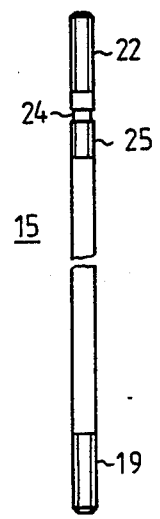
Figure 1B:
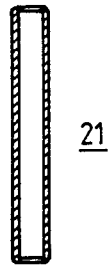
Figure 4:
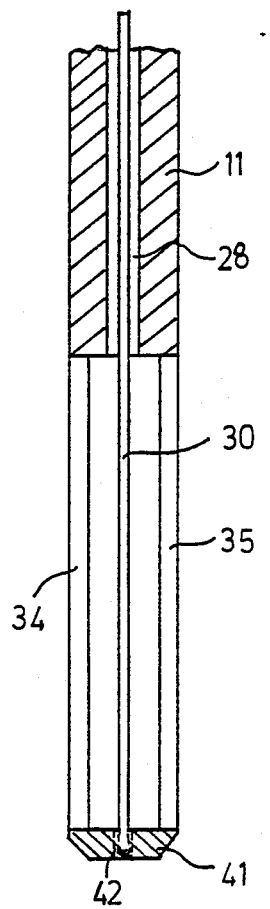
Figure 5:
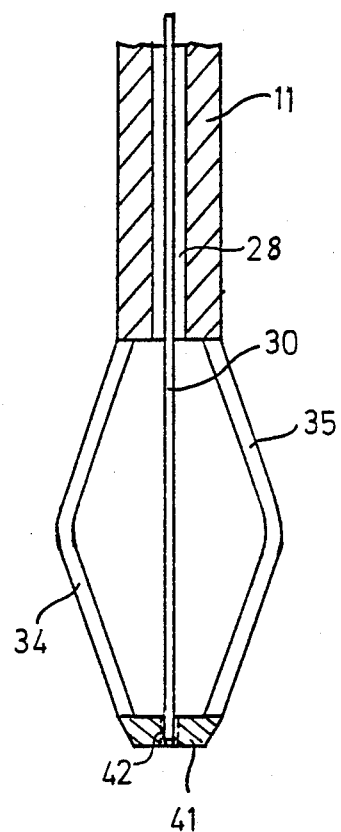

Shown are:

FIG. 1, an exemplary embodiment of a first modular assembly including a head part bearing the ball of a joint;

FIGS. 1a–1b, accessory parts of the modular assembly of FIG. 1;

FIG. 2, a modular prosthesis assembly shown partly in longitudinal section, having an end part having movable elements;

FIG. 3, an end part, seen in longitudinal section and on a larger scale, of the modular prosthesis assembly shown in FIG. 2, having movable elements capable of being spread apart;

FIG. 4, an end part, seen in longitudinal section and on a larger scale, of the modular prosthesis assembly shown in FIG. 2, having resilient elements;

FIG. 5, the end part shown in FIG. 4 with its resilient elements in the tensed state;

FIG. 6, a perspective view of an end part of a modular prosthesis assembly having movable elements capable of being spread apart in the direction counter to the direction of insertion;

FIG. 7, a cross section taken through the end part of FIG. 6, in the non-spread-apart state; and FIG. 8, the end part shown in FIG. 6, with its movable elements spread apart.

In FIG. 1, there is shown a head part 1 of a femoral prosthesis having a cone 2 for a ball of a joint that can be fitted onto the cone. On its lower end, the head part 1 has a conical bore 3, into which a protrusion 4 of an intermediate part 5, having a circular-cylindrical body 6 and a conical bore 7, can be inserted.

Fitting into the conical bore 7, in turn, is a protrusion of a further intermediate part—not shown—which is constructed substantially like the intermediate part 5 but may also have different lengths. A plurality of such intermediate parts 5 can be joined to make a shaft, as in the case of the prosthesis shown in FIG. 1.

A conical protrusion 8 of an end part 9 is insertable into the lower end of an intermediate part—namely into a corresponding conical bore 7 of the last intermediate part 5. The end part 9 has, first, a region 10 of cylindrical cross section, which is adapted to the outside cross section of the intermediate part 5 or head part 1. A conical extension 11 having a substantially cylindrically embodied shaft end 12 with a reduced diameter as compared with the intermediate part is intended for being cemented into or anchored in the medullary space. The bottom part 9 of the prosthesis also has a tongue 13 oriented at right angles to the shaft end and having bores for additionally securing the shaft. The top part 1 is provided with bores 14, which serve to secure the ligaments.

The elements 1, 5 and 9 are assembled in a conventional manner and the assembled prosthesis is implanted; optionally, the tension rod 15 has already been introduced at that time. If necessary, however, the shaft end 9 can be mounted alone, or secured with one or more intermediate parts 5, and the top part 1 finally mounted in place, and the tension rod 15 can likewise be inserted subsequently.

As an opening for the tension rod 15, the prosthesis parts 1, 5 and 9 each have through bores 16 and 17, or a blind bore 18 in the case of the bottom part 9, which are oriented axially relative to one another in the assembled prosthesis. The tension rod 15 (shown separately in FIG. 1a) is screwed with its end having a male thread 19 through the bores 16 and 17 in the top and intermediate parts, respectively, of the prosthesis, into the female thread 20 of the blind bore 18, so that it can exert tensile forces upon the bottom part 9 of the shaft prosthesis. The free end of the tension rod 15, in the inserted state, projects far enough beyond the top part of the prosthesis that—even when the sheath 21 shown in FIG. 1b is mounted on the end projecting from the top part of the prosthesis—the upper end of the tension rod 15, this end likewise being provided with a male thread 22, projects from the sheath 21.

The lower end of the sheath 21 is supported on a bearing edge 23 that surrounds the bore 16 in the top part 1 of the prosthesis and is adapted to the cross section of the sheath 21. The tension rod 15 has a restriction 24, which serves as a predetermined breaking point, in the vicinity of the end projecting from the top part 1 of the prosthesis.

The tensile forces are brought to bear upon the tension rod 15 by means of an element that is supported on the upper end 21 of the sheath. A suitable means for this purpose is a nut, which is screwed onto the male thread 22, or tongs of the type known for use with blind rivets. To enable using uniform tension rods, it is advantageous to keep sheaths 21 of different lengths on hand, which are selected in accordance with the length of the prosthesis to be prepared and that equalize the length of projection of the tension rod 15 beyond the top part 1. The set of sheaths 21 of different lengths needs to be procured only once, and also, only uniform lengths of the tension rods 15, as parts subject to wear, are required. Once the projecting end of the tension rod 15 has been detached, the conical protrusions and the bores of the prosthesis elements are sufficiently tightly joined to one another that loosening during use need not be feared. Once the sheath 21 is removed, the remaining upper end of the tension rod 15 can be grasped and loosened from the prosthesis. The region below the restriction 24 preferably has a thread 25, the spiral direction of which is contrary to the thread 19, so that a screw tool having a female thread that engages on the thread 25 will release the remaining end of the tension rod 15 from the female thread 20 of the bottom part by screw action and can be removed along with the tension rod.

To recapitulate the operation of the device as stated hereinabove, such operation involves placement of the sheath 21 over the tension rod 15 so that the bottom end of the sheath abuts bearing edge 23 and extends outwardly from the prosthesis. The tension rod extends beyond the upper end of the sheath whereby the threaded portion 22 thereof extends beyond the upper end of the sheath. The threaded portion 19 of the tension rod is threaded into threaded portion 20 of the member 9. It can now be seen that the members 1, 5 and 9 can be moved together by rotating a nut or the like on the threaded portion 2, the nut bearing against the upper edge of the sleeve and causing a compressive action to take place among the members 1, 5 and 9. When sufficient compressive movement has been achieved, the nut or the like is removed from the threaded portion 22 and the sleeve 21 is also removed for use in a different prosthetic procedure. The tension rod can be removed by rotation thereof in the opposite direction to disengage the threadedly engaged portion 19 with thread 20.

The modular prosthesis assembly shown in FIG. 2 largely corresponds to the modular prosthesis assembly of FIG. 1; the same reference numerals identify elements identical to those in FIG. 1.

The substantially cylindrically embodied shaft end 12 of the modular prosthesis assembly of FIG. 2 has movable shaft parts 32, 33 on the lower end, which can be forced apart by means of a force acting radially upon them. The radial force is effected by means of an adjusting device, which in the present exemplary embodiment is brought to bear by a wedge 40 in combination with a tension rod 15 as a tensioning element.

After the assembly of the individual elements 1, 5 and 9 of the modular prosthesis assembly, and selectively before or after implantation of the assembled prosthesis, the tension rod 15 is introduced into through bores 16, 17, 28 in the head part 1, intermediate part 5 and end part 9, the through bores 16, 17, 28 being oriented axially with respect to one another.

To this end, the tension rod 15 is screwed with its end having a male thread 19 through the bores 16, 17, 28 of the top, intermediate and end parts of the modular prosthesis assembly and into the female thread 29 of the wedge 40.

In the inserted state, the free end of the tension rod 15 projects so far beyond the head part of the modular prosthesis assembly that even with the sheath 21 mounted on the head part 1 of the modular prosthesis assembly, the upper end of the tension rod 15, which is likewise provided with a male thread, projects out of the sheath 21.

The lower end of the sheath 21 is supported on the bearing edge 23 that surrounds the bore 16 in the head part 1 of the modular prosthesis assembly and is adapted to the cross section of the sheath 21. The tension rod 15 has a restriction 24, serving as the predetermined breaking point, in the vicinity of the end projecting out of the head part 1 of the prosthesis.

Analogously to the description of FIG. 1, the tensile forces are brought to bear upon the tension rod 15 by means of an element that is supported on the upper end of the sheath 21.

With the imposition of a tensile force upon the tension rod 15, the wedge 40—as can be inferred from the enlarged cross-sectional representation of FIG. 3—presses against the inner sides 50, 51 of the movable shaft parts 32, 33, so that the head part 1 first, or the intermediate parts 5, and the bottom part 9, are firmly tightened together, so that loosening of the individual prosthesis parts during use need not be feared. If the tensile force is increased, for example by further turning the nut screwed onto the male thread 22 of the tension rod 15, then the force exerted by the wedge 40 upon the inner surfaces 50, 51 of the movable shaft parts 32, 33 causes the movable shaft parts 32, 33 to be forced radially apart. In this process, the movable shaft parts 32, 33 are forced radially apart so far that they rest firmly against the medullary cavity wall of the bone receiving the shaft.

After the projecting end of the tension rod 15 is detached, the conical protrusions and bores 3, 4, 7, 8 of the prosthesis elements 1, 5, 9 are firmly joined to one another, and the movable shaft parts rest firmly against the medullary cavity wall. After removal of the sheath 21, the remaining upper end of the tension rod 15 can be grasped and removed from the prosthesis, analogously to the description of FIG. 1. Since the wedge 40 rests firmly against the inner sides 50, 51 of the movable shaft parts 32, 33, loosening and hence yielding of the movable shaft parts 32, 33 need not be feared, and a firm seat is thus assured. Alternatively, the tension rod 15 can naturally also be left in the modular prosthesis assembly and locked in place by means of a nut that is also screwed onto the thread 25.

The shaft end 12 shown in FIGS. 4 and 5 has resilient elements 34, 35, which can be forced apart when a tensile force is exerted upon the lower ends of the resilient elements 34, 35. The lower ends of the resilient elements 34, 35 are rigidly joined to one another by a connecting element 41, which includes slits for a bayonet coupling, for example, into which the bayonet pins provided on the lower end of the tensioning element 30 can be inserted. Pulling on the tensioning element 30, which may be embodied as a thin rod, tenses the resilient elements 34, 35 into the shape shown in FIG. 5, so that in the tensed state they press against the wall of the medullary cavity.

In the embodiment of the shaft end with movable shaft parts 34, 35 shown in FIGS. 4 and 5, the tensioning element 30 can for instance by guided in a bore of the tension rod 15 as shown in FIGS. 2 and 3; the lower male thread 19 of the tension rod 15 then engages a female thread provided in the upper cone 8 of the end part 9, so that the compression of the head part 1, the intermediate part or parts 5 and the end part 9 is effected via the tension rod 15, while the forcing apart of the movable shaft parts 34, 35 is effected separately from this by means of the tensioning element 30, which with a male thread engages the female thread 42 of the connecting element 41.

Instead of a thin rod as the tensioning element 30, it is also possible to use a tension filament, which is firmly connected to the connecting element 41 and in the tensed state as shown in FIG. 5 can be secured in the vicinity of the head part 1.

In FIGS. 6–8, a further exemplary embodiment of the present invention is shown; FIG. 6 is a perspective view of this exemplary embodiment with movable shaft parts that can be unfolded out of the profile of the shaft end, while in FIGS. 7 and 8, the shaft end is shown in cross section with the movable shaft parts folded in (FIG. 7) and folded out (FIG. 8).

The inner surfaces 52, 53 of the movable shaft parts 36, 37 are spaced apart by a distance that decreases from the lower to the upper end of the lower part or shaft end 12, so that when a wedge 40 moves from the lower end toward the upper end, the movable shaft parts 36, 37 are forced apart. Since the movable shaft parts are pivotably connected in the vicinity of the lower end of the shaft end 12, the cross-sectional shape of the shaft end shown in FIG. 8 is produced in the tensed state of the movable shaft parts 36, 37. The tensile force necessary for this can be brought to bear by means of a tension filament 60, for example, by joining a screw 61, which is adjustable in a thread 62, to the tension filament 60, so that when the screw 61 is unscrewed out of the thread 62, the wedge 40 at the lower end is drawn up toward the upper end of the shaft end 12.

The unscrewing of the screw 61 can be effected by means of a separate tool, after the clamping together of the individual elements 1, 5, 9 of the modular prosthesis assembly and removal of the tension rod 15, or can be done in such a way that the tension rod 15 engages a continuous thread 18 provided in the upper cone of the end part 9, then the tensile force for joining the elements 1, 5, 9 of the modular prosthesis assembly is brought to bear upon the tension rod 15, and then the tension rod 15 is rotated further until engagement with the screw 61 is established, for example via a hexagonal protrusion and a hexagonal socket. Turning the tension rod 15 in reverse turns the screw 61 as well, which via the tension wire 60 and the wedge 40 forces the movable elements 36, 37 apart and thus effects a firm anchoring of the shaft end of the modular prosthesis assembly in the medullary canal of the bone receiving the shaft.

The invention is not limited in its scope to the preferred exemplary embodiment described above. On the contrary, a number of variants in which the provisions described are applied even to fundamentally different embodiments are conceivable.

We claim:

1. A modular assembly for a shaft prosthesis which comprises:
    (a) a head part,
    (b) an end part, one of said head part and end part having a conical protrusion and the other of said head part and end part having a conical bore, and
    (c) at least one intermediate part engagable with both said protrusion and said bore of said head part and end part and disposed between said parts, (d) said head part and said at least one intermediate part each having an aligned through bore, said end part having a bore with releasable engaging means for transmitting a force in the axial direction along said bore, the bores all being aligned axially relative to one another when said parts have been joined together, and (e) a tension rod extending through said aligned bore of each said part having an engaging element adapted to be engagable with said releasable engaging means for releasable engagement therewith, said tension rod projecting beyond said head part when said head and end parts have been joined together, said tension rod having a region of reduced cross section designed to break upon excessive tightening of said tension rod, the tensile strength of said region corresponding to a force that is sufficient to seat the connecting cones of said head, end and at least one intermediate part in such a manner that in the implanted state they are secured against loosening.

2. A modular prosthesis assembly as defined by claim 1, wherein the one of a conical protrusion and conical bore of said head part and said at least one intermediate part each have a bearing surface on the side thereof abutting each other.

3. A modular prosthesis assembly as defined by claim 2, further including a sheath slidably positioned over said tension rod to frictionally engage the bore.

4. A modular prosthesis assembly as defined by claim 1, wherein said tension rod has a male thread on its end facing said intermediate element.

5. A modular prosthesis assembly as defined by claim 1, wherein said region of reduced cross section is positioned closer to one of the ends of said tension rod and said tension rod further including a male thread at the end portion of said tension rod opposite said region of reduced cross section.

6. A modular prosthesis assembly as defined by claim 5, wherein the rotational direction for threading the thread in a tightening direction corresponds to the direction for threading the tension rod in a loosening direction.

* * * * *